United States Patent [19]
Wijesinghe et al.

[11] Patent Number: 5,832,927
[45] Date of Patent: Nov. 10, 1998

[54] SURGICAL DRAPE

[75] Inventors: Christie Wijesinghe, Partille; Kjell Zackrisson, Kållered, both of Sweden

[73] Assignee: Molnlycke AB, Gothenburg, Sweden

[21] Appl. No.: 628,620

[22] PCT Filed: Oct. 10, 1994

[86] PCT No.: PCT/SE94/00948

§ 371 Date: Apr. 9, 1996

§ 102(e) Date: Apr. 9, 1996

[87] PCT Pub. No.: WO95/10242

PCT Pub. Date: Apr. 20, 1995

[30] Foreign Application Priority Data

Oct. 11, 1993 [SE] Sweden .................................. 9303324

[51] Int. Cl.⁶ ........................................................ A61B 19/00
[52] U.S. Cl. ............................................ 128/849; 128/853
[58] Field of Search ........................................ 128/849–856

[56] References Cited

U.S. PATENT DOCUMENTS

| | | | |
|---|---|---|---|
| 3,538,912 | 11/1970 | Becker | 128/853 |
| 3,669,106 | 6/1972 | Schrading | 128/853 |
| 3,763,857 | 10/1973 | Schrading | 128/853 |
| 3,921,627 | 11/1975 | Wilson | 128/853 |
| 4,873,997 | 10/1989 | Marshall . | |
| 5,161,544 | 11/1992 | Morris . | |

*Primary Examiner*—Michael A. Brown
*Attorney, Agent, or Firm*—Young & Thompson

[57] ABSTRACT

A surgical drape including a liquid-absorbent top sheet (1) and a liquid-impermeable sheet (2) immediately beneath the top sheet. The liquid-impermeable sheet faces a patient, when the drape is in use. At least one elongated element (5) is arranged between the top sheet and the liquid-impermeable sheet.

7 Claims, 1 Drawing Sheet

SURGICAL DRAPE

FIELD OF THE INVENTION

The present invention relates to a surgical drape which includes a liquid-absorbent top sheet and a liquid-impermeable sheet which is located immediately beneath the top sheet and faces towards a patient when the drape is used.

BACKGROUND OF THE INVENTION

Applicants market a surgical drape under the registered trade name Klinidrape ® which is comprised of a three-layer laminate, a liquid-absorbent nonwoven top sheet, a liquid-impermeable polyethylene intermediate sheet, and a bottom absorbent sheet of cellulose wadding or like material. The top sheet is intended to absorb blood and other fluids that originate from the surgical area, so as to protect theatre personnel and the operating theatre against contamination. The plastic film forms a barrier against the transporation of fluid-carried bacteria between patient and the surgical area, or wound, while the layer of cellulose wadding or like material is intended to enhance patient comfort, by absorbing perspiration and preventing direct contact of the patient's skin with the plastic sheet.

When a surgical drape is placed over a patient, large areas of the drape will slope steeply in relation to the horizontal. Blood or fluid discharged from the surgical area and landing on vertically sloping parts of the drape will strive to flow down the drape under the effect of gravity, meaning that the spread of fluid absorbed by these parts of the drape will take mostly a vertical pattern. This presents a problem, since it is desirable that fluid discharged from the surgical area will be absorbed in those parts of the drape that lie closest to the surgical area, therewith reducing the risk of personnel or instruments coming into contact unintentionally with blood that has been absorbed by the absorbent material in the top sheet.

SUMMARY OF THE INVENTION

An object of the present invention is to solve this problem.

In accordance with the invention, this object is achieved with a surgical drape of the aforedefined kind which is characterized in that at least one elongated element is placed between the top sheet and the liquid-impermeable sheet. The elongated element functions as a flow barrier and forces at least part of the fluid that flows towards and against the element to change direction and flow *generally parallel with the longitudinal direction of the elongated element.

According to one preferred embodiment of the invention, each elongated element extends in a direction which is generally parallel to one edge of the surgical drape and will include absorbent material. The elongated -elements may conveniently have the form of threads consisting of absorbent fibers, such as cotton fibers or polyacrylate fibers.

BRIEF DESCRIPTION OF THE DRAWINGS

The invention will now be described in more detail with reference to an exemplifying embodiment thereof and also with reference to the accompanying drawing, in which.

DESCRIPTION OF THE PREFERRED EMBODIMENTS

Figure 1:
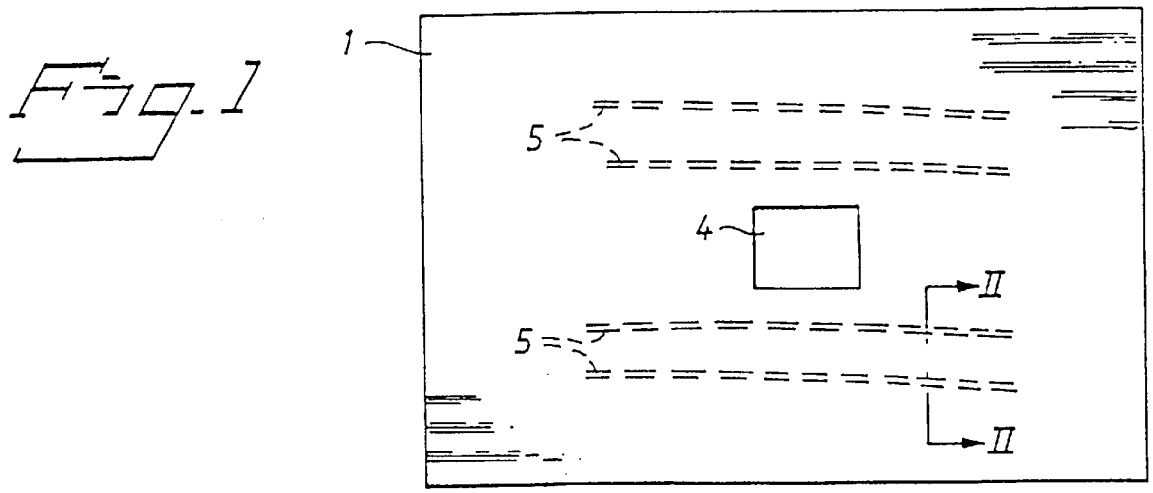
FIG. 1 illustrates schematically and from above one embodiment of an inventive surgical drape.

The illustrated surgical drape is constructed in the same way as the Klinidrape ® marketed by Applicants and includes an absorbent top sheet 1, a liquid-impermeable intermediate sheet 2, and an absorbent bottom sheet 3. The drape includes an aperture 4 which is intended to be position over the surgical area.

In the illustrated preferred embodiment of an inventive surgical drape, as shown in the Figures, threads 5 are placed between the top sheet 1 and the liquid-impermeable sheet 2, these threads extending generally parallel with two mutually opposing edges of the drape. In the illustrated case the threads 5 extend in the longitudinal direction of the drape, on either side of the aperture 4.

Figure 2:
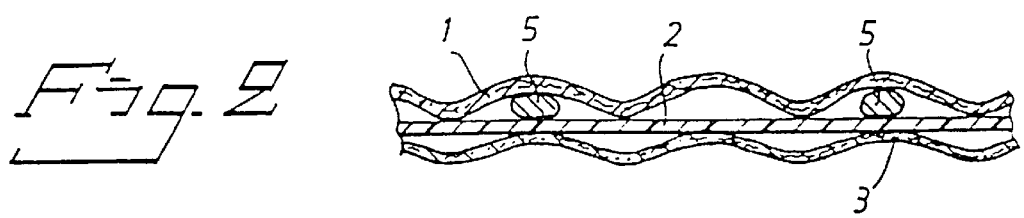
FIG. 2 is a cross-sectional view of one part of the surgical drape shown in FIG. 1.
Figure 3:
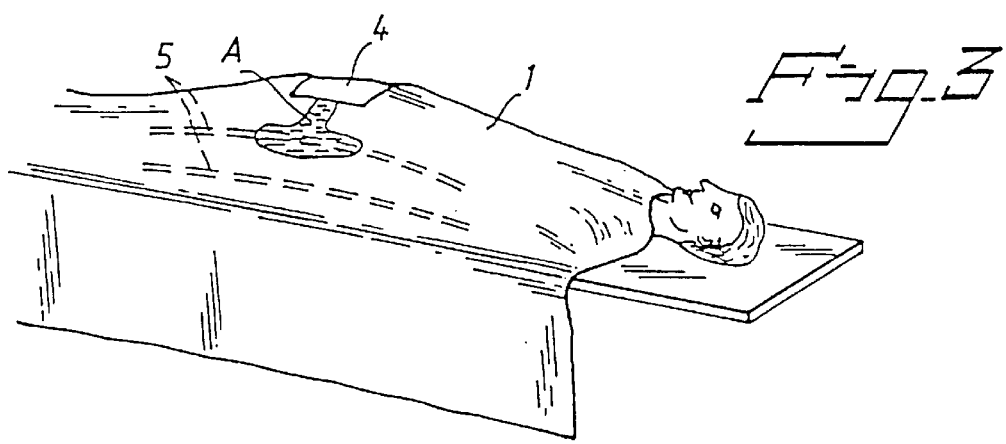
FIG. 3 illustrates the drape shown in FIG. 1 placed over a patient.

FIG. 3 shows the surgical drape of FIGS. 1 and 2 placed over a patient with the aperture 4 located over the intended surgical area, which in this case is the patient's abdominal area. Those parts of the drape which lie outside the patients sides will be inclined steeply in relation to a horizontal plane, meaning that gravity will have a significant effect on the spreading of fluid within these parts of the drape. With regard to a horizontal absorbent surface of a Klinidrape-type surgical drape, fluid will spread radially from the wetting point, so as to obtain a generally circular spread pattern, whereas fluid on a surface which is inclined to the horizontal will spread in downwards to an increasingly greater extent commensurate with the angle at which the drape parts are inclined, so as to obtain a droplet-like or pear-like spread pattern with the narrow end of the droplet facing downwards. In the case of the described surgical drape, however, the inclusion of the threads 5 will result in a spread pattern A when fluid flowing from the surgical area reaches one of the threads 5, therewith halting downward movement of the fluid and causing the fluid to flow in the longitudinal direction of the thread, as shown in FIG. 3. Should relatively large quantities of fluid be discharged from the surgical area, for instance relatively large quantities of blood or irrigation fluid, some of the fluid will probably pass beyond the upper thread of the threads 5 shown in FIG. 3, in which case this fluid will be halted by the lower of these threads. This will result in a more favorable spread pattern and enable a larger part of the absorbent surface of the drape to be active in absorbing discharged fluid.

In the case of the illustrated embodiment of the invention, the threads 5 are placed solely on those parts of the drape which lie along the sides of the patient when the drape is in position, since remaining parts of the drape will either not slope to an extent in which the spread pattern is effected to any appreciable extent by the force of gravity, or will be followed by essentially horizontal parts of the drape with a commensurate, favorable spread pattern. On the other hand, the effect of gravity may be favorable in respect of those parts of the drape that lie on the sides of the edges of the aperture that extend parallel with the transverse edges of the drape, since this will enhance spreading of the fluid in the longitudinal direction of the drape in the region of these parts. Although the threads 5 are shown to extend along only a part of the length of the drape, it will be understood that the threads may be extended along the full length of the drape if so desired.

It should be mentioned in this regard that positioning of the threads will, of course, depend upon the type of surgery concerned and that in the case of surgical drapes of other configurations intended for other types of surgery it may be appropriate to place the threads crosswise or even peripherally around the drape, in order to obtain suitable spread patterns. The number of threads used -may also vary within the scope of the invention. It is also feasible to place the threads in a checkered or diamond pattern over the whole of the drape, although only those threads which extend transversally to the flow direction will be active when the drape is in use, in accordance with the above.

The various sheets that form the aforedescribed surgical drape may be joined together by means of a regular pattern of discrete glue points and the threads 5 may be placed between the sheets 1 and 2 of the drape prior to gluing the sheets together. Thus, the threads will only be joined to the sheets 1 and 2 at one or more glue points in the glue pattern and are mainly held in position by virtue of the glue joints preventing any appreciable movement of the threads transversally in relation to their longitudinal axes. Naturally, the threads may be fastened to one or the other or both of the sheets 1 and 2 of the surgical drape.

According to one preferred variant, the threads include absorbent material meaning that the threads will have a fluid transporting function in addition to the aforesaid fluid halting and guiding function. This absorbent material may conveniently comprise fibers of so-called superabsorbent material, for instance polyacrylate fibers having a length of 60 mm and 9000 denier, these fibers being loosely bound to form a thread around which a thin reinforcing filament, for instance a nylon filament, is helically and sparsely wound.

Figure 4:
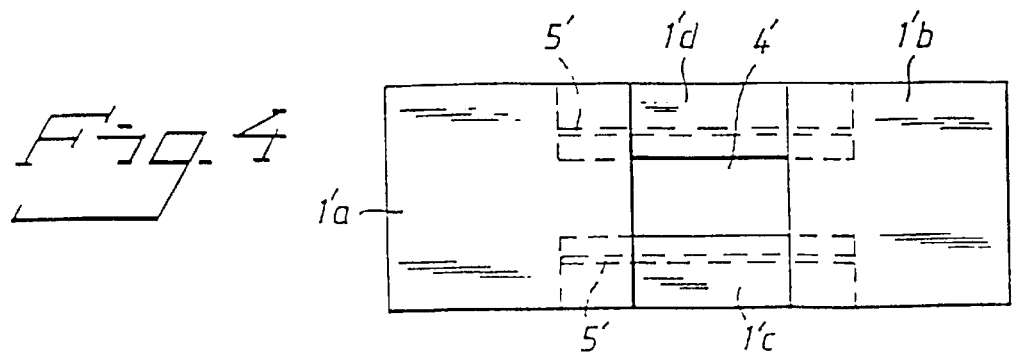
FIG. 4 illustrates an embodiment of a surgical drape which comprises four parts.

FIG. 4 illustrates a surgical drape which is comprised of four separate parts, exemplified in the Figure by the top sheet parts 1'A, 1'B, 1'c and 1'd, which have been arranged so as to form an aperture 4' in the surgical area. As will be seen from the Figure, threads 5'are arranged in the side parts 1'c, 1'd.

It will be understood that the described exemplifying embodiment can be modified in several ways without departing from the scope of the invention. For instance, elongated elements other than threads may be used, for instance strips of absorbent or non-absorbent material may be used, provided that these strips will be sufficiently flexible not to impair the drapability of the drape to any great extent. The elongated elements can also be obtained by forming folds in the top sheet. The elongated elements may also be curved instead of being straight as in the illustrated case, and need not extend parallel with the longitudinal or transverse edge of the drape. The most important thing is that those parts of the drape which are inclined to the horizontal when the drape is used extend at an angle to the force-of-gravity projection in the plane in which those parts of the drape which include the elongated elements lie. The invention can also be applied to surgical drapes which do not have an underlying absorbent comfort sheet. The invention is therefore limited solely by the contents of the following claims.

What claimed is:

1. A surgical drape, comprising:
   a liquid-absorbent top sheet;
   a liquid-impermeable sheet located immediately beneath said top sheet and facing towards a patient when said drape is being used;
   at least one separate elongated element mounted between said top sheet and the liquid-impermeable sheet, said at least one elongated element including absorbent material to halt and spread out fluid flow on the drape.

2. A surgical drape according to claim 1, wherein each elongated element (5) extends in a direction generally parallel to one edge of the surgical drape.

3. A surgical drape according to claim 1, wherein each elongated element includes a thread (5) of generally rectilinear extension.

4. A surgical drape according to claim 1, wherein each elongated element includes a thread (5) of curved extension.

5. A surgical drape according to claim 1, further comprising at least two of said at least one elongated element, wherein said sheets define an aperture, at least one elongated element (5) being arranged at each side of two opposing edges of the aperture (5) in the surgical drape, between respective edges of the aperture and corresponding edges of the surgical drape.

6. A surgical drape according to claim 1, wherein the elongated elements comprise threads 95) having absorbent fibers.

7. A surgical drape according to claim 6, wherein the absorbent fibers are polyacrylate fibers.

* * * * *